(12) United States Patent
Seabury et al.

(10) Patent No.: US 9,907,928 B2
(45) Date of Patent: Mar. 6, 2018

(54) THERAPEUTIC ENVIRONMENTAL LIGHT AND IMAGE SYSTEM

(71) Applicants: ST. PETER'S HEALTH PARTNERS, Albany, NY (US); Rensselaer Polytechnic Institute, Troy, NY (US)

(72) Inventors: George W. Seabury, Schenectady, NY (US); Robert Cella, Williamstown, MA (US); Mark Pettus, Dalton, MA (US); Dorothy Maria Urschel, Albany, NY (US); Charles Gianfagna, Albany, NY (US); Partha Dutta, Clifton Park, NY (US)

(73) Assignees: St. Peter's Health Partners, Albany, NY (US); Rensselaer Polytechnic Institute, Troy, NY (US)

( * ) Notice: Subject to any disclaimer, the term of this patent is extended or adjusted under 35 U.S.C. 154(b) by 96 days.

(21) Appl. No.: 13/723,403

(22) Filed: Dec. 21, 2012

(65) Prior Publication Data
US 2013/0165741 A1    Jun. 27, 2013

Related U.S. Application Data

(60) Provisional application No. 61/579,703, filed on Dec. 23, 2011.

(51) Int. Cl.
*A61M 21/00* (2006.01)
*A61M 21/02* (2006.01)

(52) U.S. Cl.
CPC ........ *A61M 21/02* (2013.01); *A61M 21/0094* (2013.01); *A61M 2021/005* (2013.01); *A61M 2205/053* (2013.01); *A61M 2205/52* (2013.01)

(58) Field of Classification Search
CPC .............................. A61M 21/00–21/02; A61M 2021/00–2021/0088; H05B 37/02–37/029
(Continued)

(56) References Cited

U.S. PATENT DOCUMENTS 5,343,121 A * 8/1994 Terman et al. ............... 315/158
5,589,741 A * 12/1996 Terman .............. H05B 37/0218
315/156

(Continued)

OTHER PUBLICATIONS

Keep et al., Windows in the Intensive Therapy Unit, Anaesthesia, vol. 35, Issue 3, pp. 257-262 (1980).
(Continued)

*Primary Examiner* — Catherine B Kuhlman
(74) *Attorney, Agent, or Firm* — Heslin Rothenberg Farley & Mesiti P.C.; Kristian E. Ziegler; Matthew M. Hulihan

(57) ABSTRACT

A therapeutic environmental light and image system and related methods are provided. A controller controls a lighting system and one or more images displayed on a display monitor to create a virtual window in a patient recovery room that simulates characteristics of a real window. Optionally, circadian full-spectrum light cycling is delivered via a prescriptively-selected circadian light cycle, which may or may not be configured based on the images provided on the display monitor. Additionally, ultraviolet light from an ultraviolet light source may be dosed to the patient to favorably impact biologic functions and other health aspects of the patient, to facilitate patient recovery.

16 Claims, 9 Drawing Sheets

(58) Field of Classification Search
USPC .............................................. 600/21, 26–28
See application file for complete search history.

(56) References Cited

U.S. PATENT DOCUMENTS

| | | | | |
|---|---|---|---|---|
| 6,166,496 | A * | 12/2000 | Lys et al. ....................... | 315/316 |
| 6,554,439 | B1 * | 4/2003 | Teicher ................... | F21S 8/006 |
| | | | | 315/360 |
| 2003/0014817 | A1 * | 1/2003 | Gallant et al. ..................... | 5/600 |
| 2005/0143617 | A1 * | 6/2005 | Auphan .......................... | 600/26 |
| 2007/0166671 | A1 * | 7/2007 | Walter ...................... | G09B 5/00 |
| | | | | 434/98 |
| 2008/0062323 | A1 * | 3/2008 | Visser et al. ................... | 348/596 |
| 2009/0273302 | A1 * | 11/2009 | Staats ....................... | E06B 7/28 |
| | | | | 315/297 |
| 2011/0251657 | A1 * | 10/2011 | Miyake et al. ................. | 607/88 |

OTHER PUBLICATIONS

Wilson, Larkin M., Intensive Care Delirium: The Effect of Outside Deprivation in a Windowless Unit, Archives of Internal Medicine, vol. 130, No. 2, pp. 225-226, Aug. 1972.

Ulrich, Roger S., View Through a Window May Influence Recovery From Surgery, American Association for the Advancement of Science, pp. 1-3, Apr. 27, 1984.

Walch et al., The Effect of Sunlight on Postoperative Analgesic Medication Use: A Prospective Study of Patients Undergoing Spinal Surgery, The American Psychosomatic Society, Psychosomatic Medicine, vol. 67, pp. 156-163 (2005).

Farley et al., A Room With a View: A Review of the Effects of Windows on Work and Well-Being, National Research Council Canada, Institute for Research Construction, IRC Research Report RR-136, pp. 1-33, Aug. 15, 2001, http://irc.nrc-cnrc.gc.ca/ircpubs.

Markus, Thomas A., The Function of Windows—A Reappraisal, Build. Sci., vol. 2, pp. 97-121 (1967).

Keighley, E,C., Visual Requirements and Reduced Fenestration in Offices—A Study of Multiple Apertures and Window Area, Build. Sci., vol. 8, pp. 321-331 (1973).

Roessler, G., The Psychological Function of Windows for the Visual Communication Between the Interior of Rooms with Permanent Supplementary Artificial Lighting and the Exterior, Lighting Research & Technology, vol. 12, No. 3, pp. 160-168, (1980).

Finnegan et al., Work Attitudes in Windowed vs. Windowless Environments, The Journal of Social Psychology, vol. 115, Issue 2, pp. 291-292 (1981).

Verderber, Stephen, Dimensions of Person-Window Transactions in the Hospital Environment, Environment and Behavior, vol. 18, No. 4, pp. 450-266, Jul. 1986

Verderber et al., Windows, Views, and Health Status in Hospital Therapeutic Environments, The Journal of Architectural and Planning Research, vol. 4, Issue 2, pp. 120-133 (1987).

Ne'Eman, E, Visual Aspects of Sunlight in Buildings, Lighting Research and Technology, vol. 6 No. 3, pp. 159-164 (1974).

Lusk et al., The Stress Response, Psychoneuroimmunology, and Stress Among ICU Patients, Dimensions of Critical Care Nursing, vol. 24, No. 1, Jan./Feb. 2005.

Justic, Marcia, Does "ICU Psychosis" Really Exist?, Critical Care Nurse, vol. 20, No. 3, pp. 28-37, Jun. 2000.

Divatia et al, Delirium in the ICU, Indian Journal of Critical Care Medicine, vol. 10, Issue 4, pp. 216-218, Oct./ Dec. 2006.

Gelling, Leslie, Causes of ICU Psychosis: The Environmental Factors, Nursing in Critical Care, pp. 22-26, vol. 4, No. 1 (1999).

Lasater et al., Postcardiotomy Psychosis: Indications and Interventions, Heart & Lung, Psychological Aspects of Critical Care, vol. 4, No. 5, pp. 724-729, Sep.-Oct. 1975.

Mohta et al., Psychological Care in Trauma Patients, Injury, International Journal of the Case of the Injured, vol. 4, No. 1, pp. 17-25 (2003).

Easton et al., Sensory-Perceptual Alterations: Delirium in the Intensive Care Unit, Heart and Lung, The Journal of Critical Care, vol. 17, Issue 3, pp. 229-237 (1988).

Patrick, Pamela, K.S., Burnout: Job Hazard for Health Workers, Hospitals, The Human Ingredient, pp. 87-90, Nov. 16, 1979.

Mealer et al., Increased Prevalence of Post-Traumatic Stress Disorder Systems in Critical Care Nurses, American Journal of Respiratory Critical Care Medicine, pp. 693-697, vol. 175 (2007).

Maloney, Joseph P., Job Stress and Its Consequences on a Group of Intensive Care and NonIntensive Care Nurses, Advances in Nursing Science, vol. 2, No. 2, pp. 31-42, Jan. 1982.

Gibbons et al., Biomedical Equipment in the Neonatal Intensive Care Unit: Is it a Stressor?, Journal of Prenatal and Neonatal Nursing, vol. 12, No. 3, pp. 67-73 (1988).

Bailey et al., The Stress Audit: Identifying the Stressors of ICU Nursing, Journal of Nursing Education, vol. 19, No. 6, pp. 15-25, Jun. 1980.

Coomber et al., Stress in UK Intensive Care Unit Doctors, British Journal of Anaesthesia, vol. 89, pp. 873-881 (2002).

Firth-Cozens, Jenny, Individual and Organizational Predictors of Depression in General Practitioners, British Journal of General Practice, pp. 1647-1651, Oct. 1998.

Goodfellow et al., Staff Stress on the Intensive Care Unit: A Comparison of Doctors and Nurses, Anaesthesia, vol. 52, pp. 1037-1041 (1997).

Lawton et al., Ecology and the Aging Process, In: The Psychology of Adult Development and Aging (ed: Carl Eisdorfer and M. Powell Lawton), pp. 619-674 (1973).

Ely et al., The Impact of Delirium in the Intensive Care Unit on Hospital Length of Stay, Intensive Care Med., vol. 27, pp. 1892-1900 (2001).

Hegarty et al., Using Multimedia Technology to Help Combat the Negative Effects of Protective Isolation on Patients: The Open Window Project-An Engineering Challenge, Journal of Visual Communication in Medicine, vol. 32, Nos. 3-4, pp. 72-77, Sep.-Dec. 2009.

Fontaine et al., Designing Humanistic Critical Care Environments, Critical Care Nursing Quarterly, Planning and Design, vol. 24, Issue 3, pp. 21-34, Nov. 2001.

Devlin, et al., Health Care Environments and Patient Outcomes: A Review of the Literature, Environment and Behavior, vol. 35, No. 5, pp. 665-694, Sep. 2003, http://eab.sagepub.com/content/35/5/665.

Kaplan, Rachel, The Nature of the View From Home, Psychological Benefits, Environment and Behavior, vol. 33, No. 4, pp. 507-542, Jul. 2001.

Meyer et al., Adverse Environmental Conditions in the Respiratory and Medical ICU Settings, Chest, vol. 105, No. 4, pp. 1211-1216, Apr. 1994, http://jupcvss.chestpubs.org.

Küller et al., The Impact of Light and Colour on Psychological Mood: A Cross-Cultural Study of Indoor Work Environments, Ergonomics, vol. 49, No. 14, pp. 1496-1507, Nov. 15, 2006, http://www.tandf.co.uk/journals.

Penn et al., Virtual Enriched Environments in Paediatric Neuropsychological Rehabilitation Following Traumatic Brain Injury: Feasibility, Benefits and Challenges, Developmental Neurorehabilitation, vol. 12, No. 1, pp. 32-43, Feb. 2009.

Bergeron et al., Intensive Care Delirium Screening Checklist: Evaluation of a New Screening Tool, Intensive Care Medicine, vol. 27, pp. 859-864 (2001).

Wesley et al., Delirium in Mechanically Ventilated Patients, Validity and Reliability of the Confusion Assessment Method for the Intensive care Unit (CAM-ICU), The Journal of the American Medical Association, vol. 286, No. 21, pp. 2703-2710, Dec. 5, 2001 (reprinted).

Shepley, Mardelle McCuskey, Research on Healthcare Environments for Children and Their Families, International Academy for Design and Health, pp. 227-240 (available at http://www.designandhealth.com/uploaded/documents/Publications/Papers/Mardelle-McCuskey-Shepley-WCDH2000, last accessed Sep. 12, 2013).

(56) References Cited

OTHER PUBLICATIONS

Turner, Missy, Virtual Windows Brighten Rooms Without a View, Houston Business Journal, pp. 1-4, Sep. 23, 2001, http://www.bizjournals.com/houston/stories/2001/09/24/focus1.html.

Dunn et al., Nighttime Lighting in Intensive Care Units, Critical Care Nurse, vol. 30, No. 3, pp. 31-37, Jun. 2010.

Shepley, M. McCuskey, The Role of Positive Distraction in Neonatal Intensive Care Unit Settings, Journal of Perinatology, vol. 26, pp. S34-S37 (2006).

Kahn et al., A Plasma Display Window?—The Shifting Baseline Problem in a Technologically Mediated Natural World, Journal of Environmental Psychology vol. 28, pp. 192-199 (2008).

Aldemir et al., Research Article, Predisposing Factors for Delirium in the Surgical Intensive Care Unit, Critical Care, vol. 5, pp. 265-270 (2001).

Adam et al., ABC of Intensive Case, Other Supportive Care, Clinical Review, British Medical Journal, vol. 319, pp. 175-178, Jul. 17, 1999.

Girard et al., Delirium in the Intensive Care Unit, Critical Care, vol. 12 (Suppl. 3), pp. 1-9, May 14, 2008 (available at: http://ccforum.com/content/12/S3/S3).

Wiley, Jonh P., Jr.,J. Help Is on the Way, Smithsonian Magazine, vol. 30, No. 4, pp. 22-23, Jul. 1999, (available at: http://www.smithsonianmag.com/people-places/phenom_jul99.html#ixzz2VRzCHqcd).

\* cited by examiner

THERAPEUTIC ENVIRONMENTAL LIGHT AND IMAGE SYSTEM

BACKGROUND

Fluctuations in exposure to light and imagery can profoundly modulate biologic systems. As an example, evidence demonstrates a connection between exposure to natural light and positive health benefits. Exposure to light can contribute beneficially to patient health by counteracting symptoms of seasonal affective disorder, improving resistance against onset of sepsis, and facilitating rapid and efficient patient treatments, mood adjustments, and circadian rhythm control, among other contributions. What is needed is a system to facilitate hospital patient recovery through the controlled exposure to selected light conditions, for instance when provision of natural light to a patient is not an available option.

BRIEF SUMMARY

The shortcomings of the prior art are overcome and additional advantages are provided through the provision of a system, method, and computer program product to facilitate healing of a patient.

In one aspect, a therapeutic cognitive environmental psycho-physiological image and light system is provided. The system includes, for instance, a patient recovery room; a display monitor within the patient recovery room; a lighting system providing lighting of variable characteristics within the patient recovery room; an image generator in communication with the display monitor to display at least one image on the display monitor; and a controller coupled to the lighting system and one or more of the image generator or the display monitor, the controller controlling the at least one image displayed on the display monitor and controlling the lighting system to control lighting within the patient recovery room, wherein the controlling by the controller varies the lighting within the patient recovery room across a period of time.

In another aspect, a method is provided which includes providing within a patient recovery room a display monitor, a lighting system providing lighting of variable characteristics within the patient recovery room, and an image generator in communication with the display monitor to display at least one image on the display monitor; and providing a controller coupled to the lighting system and one or more of the image generator or the display monitor, the controller controlling the at least one image displayed on the display monitor and controlling the lighting system to control lighting within the patient recovery room, wherein the controller varies the lighting within the patient recovery room across a period of time.

In a further aspect, another method is provided which includes, for instance, controlling at least one image displayed on a display monitor across a period of time, the display monitor provided within a patient recovery room, wherein controlling the at least one image comprises controlling an image generator in communication with the display monitor; controlling, by a processor, a lighting system providing lighting of variable characteristics within the patient recovery room, wherein controlling by the processor varies the lighting within the patient recovery room across the period of time; and wherein controlling the at least one image and controlling the lighting system controls light provided within the patient recovery room to facilitate patient healing of a patient within the patient recovery room.

In yet a further aspects, a computer program product is provided for facilitating healing of a patient, the computer program product including a non-transitory storage medium readable by a processor and storing instructions for execution by the processor to perform a method including controlling at least one image displayed on a display monitor across a period of time, the display monitor provided within a patient recovery room, wherein controlling the at least one image comprises controlling an image generator in communication with the display monitor; controlling a lighting system providing lighting of variable characteristics within the patient recovery room, wherein controlling the lighting system varies the lighting within the patient recovery room across the period of time; and wherein controlling the at least one image and controlling the lighting system controls light provided within the patient recovery room to facilitate patient healing of a patient within the patient recovery room.

Additional features and advantages are realized through the techniques of the present invention. Other embodiments and aspects of the invention are described in detail herein and are considered a part of the claimed invention.

BRIEF DESCRIPTION OF THE SEVERAL VIEWS OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

A therapeutic environmental light and image system is disclosed herein. In one example, the therapeutic environmental light and image system comprises a therapeutic cognitive environmental psycho-physiological image system. The system provides, in part, a virtual window that can simulate sensory perception characteristics of a real window to thereby replicate the presence of the real window. Such a system may be particularly useful when a patient's location is prohibitive of adequate exposure to natural light, for instance when patient recovery occurs, at least in part, in a windowless patient recovery room. Optionally, circadian full-spectrum light cycling and individualized guided imagery are delivered to powerfully augment neurotransmitter balance, immunomodulatory function, autonomic tone, gastrointestinal integrity, and oxidative stress, as examples. This can favorably impact biologic functions and other health aspects including cognition (e.g. reduce delirium risk), ventilator-associated risks, infection risk, medication use, mortality, and patient length of stay. Additionally, the use of full-spectrum light in therapeutic doses facilitates the conversion of vitamin D in the skin, providing further health benefits to the patient. While aspects of the invention are described with respect to a hospital setting, settings other than hospitals will benefit from the present invention, as will be apparent to those having ordinary skill in the art.

Figure 1:
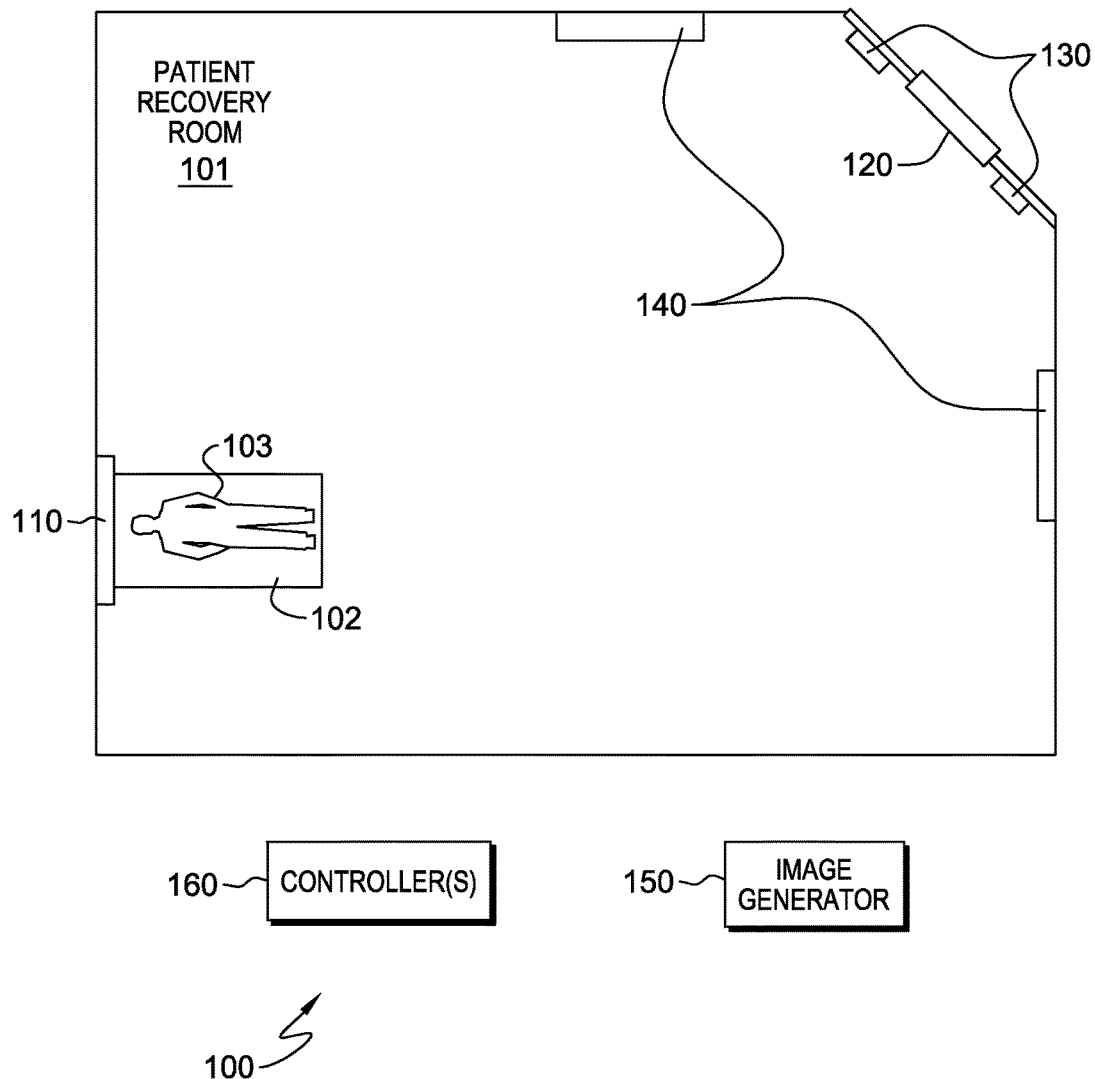
FIG. 1 depicts one example of a therapeutic cognitive environmental psycho-physiological image and light system, in accordance with one or more aspects of the present invention.

In accordance with one or more aspects of the present invention, a therapeutic cognitive environmental psycho-physiological image and light system is provided, an example of which is depicted in FIG. 1. Therapeutic cognitive environmental psycho-physiological image and light system 100 (referred to as 'system 100') is provided in a hospital setting, in this example, to facilitate recovery of a hospital patient. System 100 includes patient recovery room 101 having patient bed 102 for hospital patient 103. In this example, patient recovery room 101 also includes an ultraviolet (UV) light source 110. UV light source 110 is positioned proximate patient 103 to deliver, in one example, controlled UV light dosages to patient 103. UV light source 110 is mounted on, or just above, patient bed 102, and is sufficiently close to patient 103 to deliver and facilitate the absorption of UV light in concentrations tailored to induce a desired level of Vitamin D production in the skin of patient 103, which, in turn, is known to promote patient healing.

Within patient recovery room 101 (e.g. mounted in/on a ceiling or wall thereof) is display monitor 120 for displaying one or more images within the room. Also included in patient recovery room 101 is a lighting system that includes, in this example, outdoor lighting simulation system 130 and variable intensity ambient lighting system 140. Display monitor 120, outdoor lighting simulation system 130, and variable intensity ambient lighting system 140 are controllable to provide desired lighting characteristics (e.g. conditions and images) within patient recovery room 101, as is described in further detail below.

Also included as part of system 100 is image generator 150, which provides one or more images for display on display monitor 120. Additionally, one or more controller(s) 160 are included in system 100 to control one or more of UV light source 110, display monitor 120, outdoor lighting simulation system 130, variable intensity ambient lighting system 140, and image generator 150.

In system 100, static and/or dynamic images are displayed on display monitor 120 simultaneous to, and in conjunction with, the delivery of visible light of desirable power, density, and function from outdoor lighting simulation system 130 and variable intensity ambient lighting system 140. Controlled light exposure can stimulate, manage, and control sensory perceptions of patient 103 within patient recovery room 101. Desired lighting conditions are delivered within patient recovery room 101, and, in one example, these lighting conditions are based on a prescriptively-selected circadian rhythm cycle to influence and selectively adjust ("entrain) the natural circadian cycle of patient 103.

The lighting conditions provided in patient recovery room 101 cooperate with the one or more images displayed on display monitor 120 to promote patient recovery by stimulating and modulating the patient's biologic systems. In this regard, system 100 creates the flow environmental experience of a room having a real window (positioned at the location of display monitor 120 and surrounding outdoor lighting simulation system 130). To ensure continued operation, the components may be provided with backup power by a backup power source (not pictured). System 100 can thereby provide a continual (24 hours a day, 7 days a week) impression of a real window in patient recovery room 101, including the impression that the lighting in the patient recovery room 101 is natural light entering the patient recovery room through this 'real' window.

Figure 2:
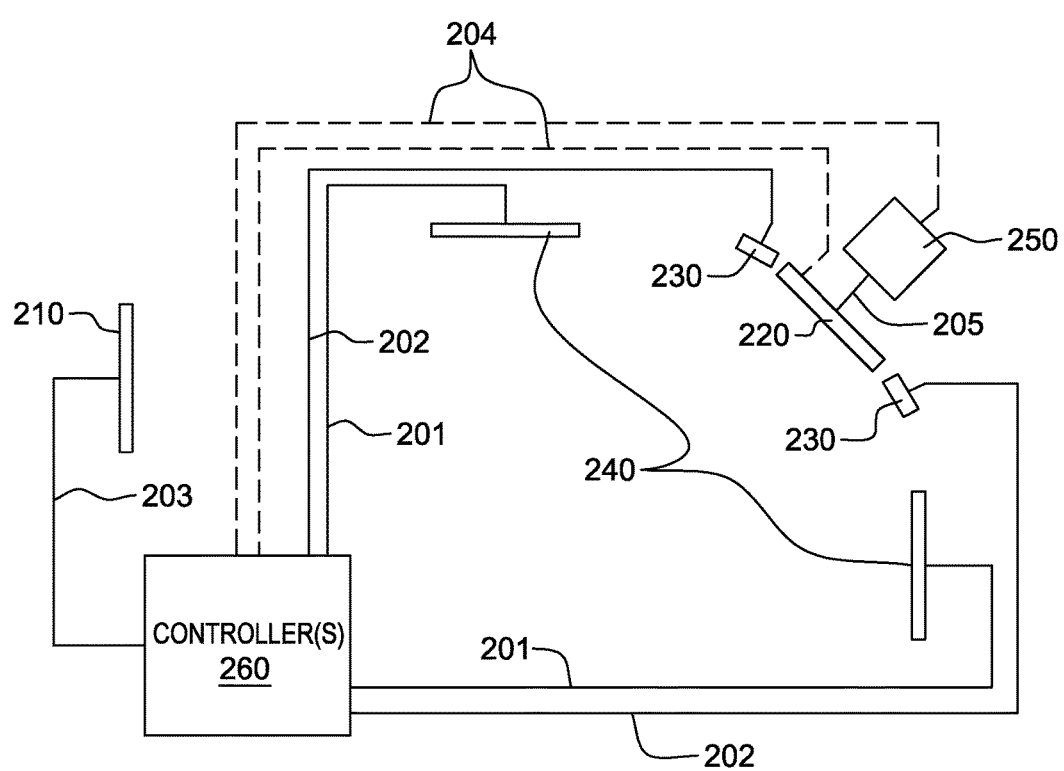
FIG. 2 depicts one example of a communication configuration between components of the system of FIG. 1, in accordance with one or more aspects of the present invention.

To accomplish these and other objectives, controller(s) 160 are provided and configured to control components of imaging system 100 via configured communications paths. FIG. 2 depicts one example of a communication configuration between components of therapeutic cognitive environmental psycho-physiological image and light system 100 of FIG. 1. In FIG. 2, controller(s) 260 communicate with variable intensity ambient lighting system 240 and outdoor lighting simulation system 230 via communications paths 201 and 202, respectively. Controllers 260 additionally communicate with UV light source 210, if provided, via communication path 203.

Communication across a communication path includes unidirectional and/or bidirectional communication. Communication can include commands and/or directions communicated between the controller and the component with which the controller communications, for example commands issued by the controller and performed by the component, with the result that the controller controls operation of the component. In one embodiment, controller 260 controls display monitor 220, control which images are displayed on display monitor 220, and control the lighting system components (e.g. outdoor lighting simulation system 230 and/or variable intensity ambient lighting system 240) to control light within the patient recovery room, as described below. Thus, communication between controller 260 and other components includes the passage of data between the two components, for instance data including or describing images and/or light field characteristics to be provided in the patient recovery room. Additionally, controller 260 can control UV light source 210 to control the discharge of UV light from UV light source 210.

Communications path 205 extends between display monitor 220 and image generator 250. Controller 260 may optionally be in communication with image generator 250 and/or display monitor 220 via one or more communications paths 204. In one embodiment, controller 260 is in communication with one of image generator 250 or display monitor 220, while in another embodiment, controller 160 is in communication with both image generator 250 and display monitor 220 and optionally controls aspects of operation of both components.

A communications path can comprise any suitable communication path for communications between components, as will be appreciated by one having ordinary skill in the art. It can include one or more digital or analog connections operating via wired or wireless (or a combination thereof) technology to facilitate communication between components. As non-limiting examples, it can include a direct connection or path between two components, or it can include a series of interconnections, for instance network connections such as a local area network (LAN), a wide area network (WAN), a token ring, or Ethernet connections utilizing routers, switches, and/or hubs. When a communication path incorporates wireless communication, any suitable wireless technology can be employed. By way of specific examples, wireless connection technology such as RF, Wi-Fi, WLAN, Bluetooth, ZIGBEE, or any other suitable wireless communication protocol and supporting hardware may be employed.

The communications path could comprise audio and/or video connections for passing audio and/or video between the components. For instance, display monitor 220 may receive one or more images for display via a video connection such as a composite, component, S-Video, VGA, or HDMI video connection, as examples. When a communication path extends from/to a component, it should be understood to include the possibility that the communication path extends from/to a sub-component of that component.

In the example of FIG. 2, image generator 250 is depicted as a separate component. In an alternate embodiment, image generator 250 is a sub-component of a controller 260. In that case, display monitor 220 communicates with the controller 260 via a communications path extending between display monitor 220 and controller 260, or alternatively display monitor 220 communicates directly with the image generator as a sub-component of controller 260, via a communication path extending between display monitor 220 and image generator 250.

Figure 3:
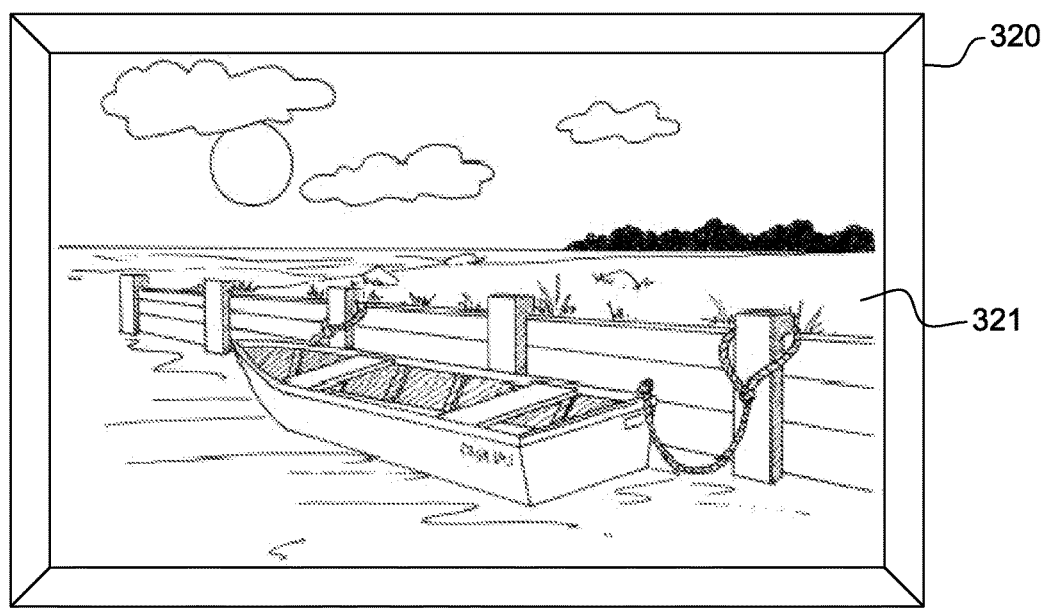
FIG. 3 depicts one example of a display monitor for displaying images in accordance with one or more aspects of the present invention.

The display monitor is configured to display one or more images in a patient recovery room, such as room 101 described above in connection with FIG. 1. The display monitor can be mounted in the patient recovery room in any appropriate orientation (e.g. vertically, horizontally) and location. Further detail of a display monitor is provided with reference to FIG. 3, which depicts one example of a display monitor for displaying one or more images in accordance with one or more aspects of the present invention. In FIG. 3, display monitor 320 comprises a high-brightness display panel. Examples of technology for implementing display monitor 320 include flat panel liquid crystal display (LCD), rear projection, such as using micro-tiles (Digital Light Processing) technology, or front-projection. Rear projection using micro-tiles (DLP technology) may be desirable when a larger coverage area and when higher light output is desired. Other display monitor technologies are also possible.

Display monitor 320 can optionally be provided with trim and other components to enhance the impression that display monitor 120 is part of a real window. For instance, a window casing can optionally be provided to partially or wholly surround or encase display monitor 320. Curtain(s), shade(s), and/or valance(s) may further be provided, if desired. Such an example is depicted and described with reference to FIG. 10.

In operation, display monitor 320 receives and displays one or more aesthetically pleasing images from an image provider, such as an image generator (150 or FIG. 1) and/or a controller (160 of FIG. 1). This set of images can include static images and/or dynamic images. In the example of FIG. 3, a single aesthetically pleasing image 321 of a beach is displayed, however in other examples, the set of images comprises multiple images and/or a video displaying a scene.

The set of images displayed on the display monitor are selected by, for instance, the patient or by a medical practitioner, or automatically selected by a controller. In one example, the set of images comprises a real-time video feed provided from camera(s) positioned at an external location (such as one the outside of a hospital building).

The set of images may be selected from a plurality of aesthetically pleasing images or sets of images, which are selectively providable to the patient depending on a treatment plan and/or patient preference, as examples. The sets of images are tailored (or can be tailored through manipulation, as described below) to respective circadian rhythm cycles, and thus may differ in image content from each other.

In one embodiment, as a set of images is displayed on the display monitor over a period of time, such as over approximately 24 hours, the lighting conditions of the scenes depicted in those images, which lighting conditions can include sunrise and sunset at a location depicted in the images on the display monitor, can be mimicked by the outdoor lighting simulation system and/or the variable intensity ambient lighting system, so that the lighting conditions provided within the patient recovery room are consistent with (i.e. provide) the lighting conditions depicted in the images displayed on the display monitor. These lighting conditions can follow a circadian rhythm cycle which may be selected prescriptively to be provided to the patient. To mimic the changing lighting conditions, the outdoor lighting simulation system and variable intensity ambient lighting system utilize capabilities thereof to change one or more of the color, intensity, brightness, direction, etc. of light emitted therefrom.

In another example, the lighting conditions to be provided in the patient recovery room are selected first, for instance by means of specifying or selecting a circadian rhythm cycle to be provided in patient recovery room 101, and then an appropriate set of images may be automatically selected based on similarities between the lighting characteristics of those images and the lighting conditions to be provided in the patient recovery room. Alternatively or additionally, the images for display are selected by the patient and then the images are automatically modified and altered, for instance by an image processing facility (such as image filtering software), if necessary, so that the lighting characteristics depicted in the images conform to the desired lighting characteristics for the patient recovery room based on the specified or selected circadian rhythm cycle. In either case, the selected circadian rhythm cycle representing the lighting pattern to be provided in the patient recovery room is chosen, and this dictates the lighting conditions to be provided by the outdoor lighting simulation system and/or variable intensity ambient lighting system. Then, the appropriate images are displayed at the appropriate times so that the lighting characteristics presented in the images corresponds to the lighting characteristics delivered by the outdoor lighting simulation system and/or variable intensity ambient lighting system.

Figure 4:
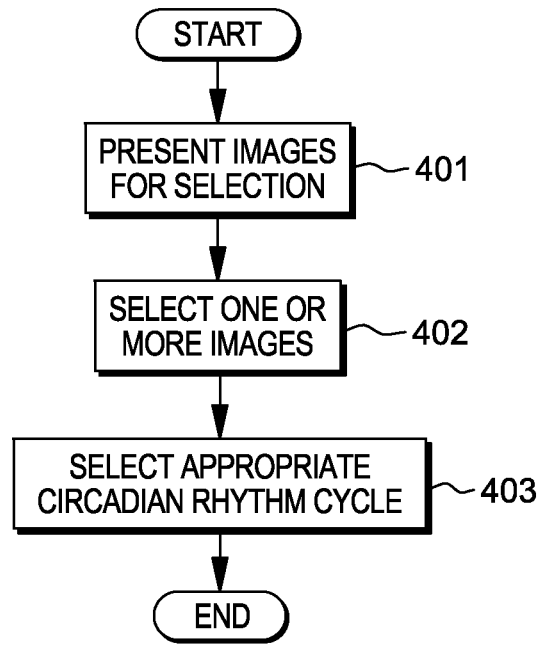
FIG. 4 depicts one example of a process for selecting an image and circadian rhythm cycle program for providing within a patient recovery room, in accordance with one or more aspects of the present invention.

FIG. 4 depicts one example of a process for selecting an image and circadian rhythm cycle program for providing within the patient recovery room. One or more controllers can facilitate this selection by, for instance, providing in interface usable by a user to select and/or specify the program. The process begins by presenting images for selection, 401. The images may be aesthetically pleasing images that are arranged into different scenes, with each scene comprising multiple images. Alternatively or additionally, the images may comprise a mixture of videos (or dynamic images) and static images, as examples. Next, one or more images are selected, 402. They can be selected by a patient and/or medical professional, and this can be based on patient preferences, for instance. Further, an appropriate circadian rhythm cycle is selected, 403. In one example, the appropriate circadian rhythm cycle is selected prescriptively by a medical professional, either directly or indirectly. Examples of direct selection of a circadian rhythm cycle include selection from a plurality of pre-defined circadian rhythm cycles presented to the medical practitioner, or explicitly defining/inputting a desired circadian rhythm cycle by the medical professional. Alternatively, the circadian rhythm light cycle could be indirectly selected by the medical professional by specifying a patient goal or recovery treatment plan, which is used by the controller and/or other components of the system to automatically select or define an appropriate circadian rhythm cycle responsive to specifying the patient goal or treatment plan. In yet another embodiment, the selection of the circadian rhythm cycle can be a combination of the above, wherein the medical professional inputs a patient goal or treatment plan and the system provides, in response to and based on the input goal or treatment plan, one or more appropriate or suggested circadian rhythm cycles for selection by the medical professional and/or patient. As part of the selecting the appropriate circadian rhythm cycle, a prescriptive UV dosage schedule can be automatically or manually selected/specified for supplying UV light dosage to be provided to the patient via a UV light source, if desired.

Figure 5:
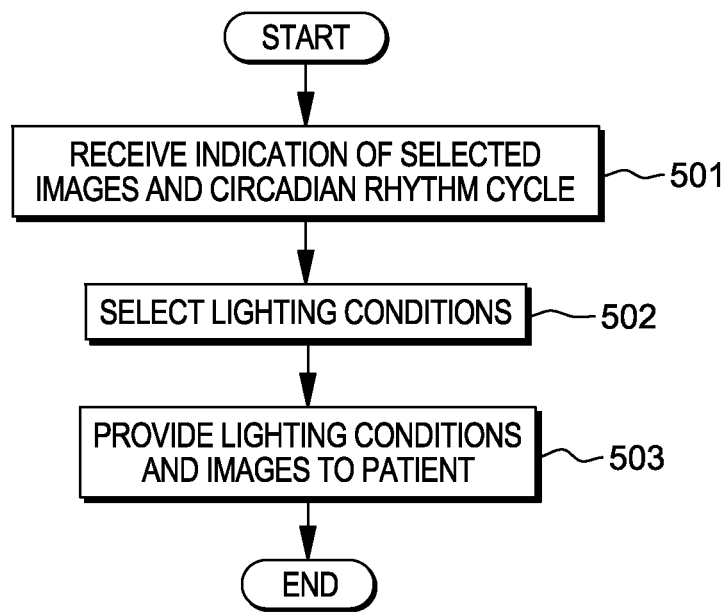
FIG. 5 depicts one example of a process for delivering lighting and images within a patient recovery room according to a selected image and circadian rhythm cycle program, in accordance with one or more aspects of the present invention.

After selection of an image and circadian rhythm cycle program (FIG. 4), the controller performs a process in which the image and circadian rhythm cycle program is executed to deliver lighting and imagery within the patient room based on the selected image and circadian rhythm cycle program. One example of such a process is depicted in FIG. 5. The process begins when one or more controller(s) receive indication(s) of the selected images and the selected circadian rhythm light cycle, 501. For instance, these indication(s) are received as input from the patient and/or medical professional. Next, the controller(s) select lighting conditions based on the selected images and/or circadian rhythm cycle, 502. The lighting conditions and images are then provided to the patient within the room, 503, by controlling the lighting system (e.g. outdoor light simulation system and/or variable intensity ambient lighting system) while displaying the selected one or more images, as is described in further detail below. Providing the lighting conditions and images to the patient within the room is performed continually during the duration of the circadian rhythm cycle.

By way of specific example, suppose a patient is newly admitted to a patient recovery room for recovery. The patient is presented with several different scenes of aesthetically pleasing vistas, each scene including a plurality of images, some of which are included within a video. The patient selects a beach scene, such as that depicted in FIG. 3. The beach scene includes dynamic images depicting a continuous scene of that beach throughout a time period of 24 hours. The images include images having various lighting conditions such as sunrise, mid-day, sunset, and dim moonlight, as well as other environmental conditions such as weather progression, animal patterns, wave, and tidal movements of the ocean, etc. Also selected, prescriptively and by a medical professional, or automatically, is an appropriate circadian rhythm cycle to be implemented within the room and delivered to the patient. Suppose that the particular circadian rhythm cycle specifies a 24-hour light/dark cycle with sunrise at 6:15 AM and sunset at 8:00 PM.

Using this example, the outdoor lighting simulation system and variable intensity ambient lighting system continually deliver, during this circadian rhythm cycle, changing lighting conditions within the patient recovery room that continuously mimic the lighting conditions of the selected scene (set of images) over the 24 hour light-dark cycle. The lighting systems accomplish this by continuality adjusting the characteristics of light emitted therefrom. Taking the start of the cycle to be 12:00 AM, the lighting conditions depicted in the images from about 12:00 Am to about 6:15 AM, and provided within the patient recovery room during this time, will be mostly darkness with dim moonlight. As the 6:15 AM sunrise approaches, the images displayed on the display monitor will depict the progression of the sunrise, including the change in direction, intensity, and color of the light coming from the sun (which may or may not appear in the beach scene itself). During the sunrise, the outdoor lighting simulation system and variable intensity ambient lighting system will gradually adjust the lighting in the patient recovery room to mimic these progressing lighting conditions of the sunrise depicted in the images of the scene. Controlling the lighting conditions in the room will give the impression (to those within the room) that natural lighting from the sunrise in the depicted images is entering through a window positioned at the display monitor. As the sunrise in the scene progresses, the outdoor lighting simulation system and variable intensity ambient lighting system will cooperate to alter the lighting in the patient recovery room to mimic the changing lighting conditions of this progression. For instance, the variable intensity ambient lighting system will gradually provide light of increasing intensity that would be experienced during the sunrise at the beach in the beach scene, while the outdoor lighting simulation system will gradually adjust the intensity, direction, and/or color of simulated sunlight emitted therefrom and entering the room from the area of the display monitor' which serves as a virtual window looking out at the beach scene. These changing lighting conditions occur continuously, cooperating with the lighting conditions in the displayed images.

Eventually, as noontime approaches and passes, the lighting conditions in the room will mimic this as well. The variable intensity ambient lighting system will adjust the intensity of the light emitted therefrom, while the outdoor lighting simulation system will adjust the intensity and direction of the simulated sunlight that it emits. In this manner, the outdoor lighting simulation system is a sunlight simulation system. It may, for instance, gradually adjust the direction of the light emitted from the sunlight simulation system to simulate the sunlight emitted by the sun passing through its highest position in the sky. Meanwhile, the images of the scene on the display monitor will depict such lighting at the beach in the beach scene. As the 24 hour period continuously progresses, so too will the images on the display monitor and the lighting conditions provided within the room, in cooperation with each other, through precise control of the lighting emitted from the lighting systems. As 8:00 PM (sunset) passes, the images will gradually depict the sunset, while the lighting systems mimic the lighting conditions of the sunset. The lighting will gradually become less intense and the outdoor lighting simulation system will simulate a sunset by adjusting the direction of simulated sunlight, along with intensity and other characteristics of the simulated sunlight, such as color. After sunset, the lighting conditions will have changed to mostly darkness with dim moonlight, as indicated by this selected circadian rhythm cycle. The nighttime lighting conditions progress until 12:00 AM when the cycle can repeat or a different or altered circadian rhythm cycle having different lighting conditions can commence.

Thus, the lighting conditions provided within the room continuously change with the passage of time as a result of controlling the variable intensity ambient lighting system and the sunlight simulation lighting system. Further details about the variable intensity ambient lighting system and the outdoor lighting simulation system are provided below with respect to FIGS. 6 & 7.

From the above, it is seen that the display monitor depicts images during the cycle that coincide with the lighting conditions delivered in the room during this cycle, and vice versa. In one example, a single image of the beach scene is displayed while the image or display monitor is continuously adjusted by filters or other image processing to mimic the continually changing lighting conditions in the patient recovery room as the period of time passes through simulated darkness, sunrise, sunset, and back to darkness (and all periods therebetween), so that it appears as though the lighting changes are also occurring in the image of the beach scene.

In another example, rather than making adjustments to the images or display monitor, several images or a video can be taken at the beach scene as it undergoes real natural lighting condition changes, and those images/video are displayed on the display monitor for the patient. In this example, other environmental conditions such as weather conditions, animal patterns, wave and tidal movements of the ocean, will also be depicted over the period of time. In addition, if a UV light dosage prescription is provided by the medical professional, the UV light source can be controlled over the period of time to deliver the proper dosage and dose schedule. This dosage can coincide with UV light amounts the patient would have experienced if the patient were at the physical location depicted in the images, or at least would have experienced if sitting behind a window that was physically located at the physical location depicted in the images. Alternatively, the UV light doses can be independent of the images and/or lighting conditions within the patient recovery room.

The coordinated imagery and light conditions facilitate, in one example, entrainment of the patient to the selected circadian rhythm cycle. This in turn facilitates healing of the patient. Entrainment of the patient to the selected circadian rhythm cycle refers to the process of training the patient's circadian rhythm (internal "biologic clock") to the selected circadian rhythm cycle, which typically occurs over the course of days or weeks.

As noted, in one example, a desired circadian rhythm cycle is selected first, and then the lighting characteristics to be provided in the patient recovery room are selected responsive to this selection of the circadian rhythm cycle. The circadian rhythm cycle to which the patient should be exposed can be selected or specified by a medical professional based on a desired treatment plan to provide therapeutic benefits to the patient. The circadian rhythm cycle can be selected from a plurality of pre-programmed circadian rhythm cycles available for selection. Alternatively, a customized circadian rhythm cycle can be specified by creating a new circadian rhythm cycle or modifying one of the existing circadian rhythm cycles, in order to fit the particular circumstances of patient recovery.

After a circadian rhythm cycle is selected, the controller(s) control one or more components in order to provide imagery and lighting in the patient recovery room that conform to the selected circadian rhythm cycle.

Figure 6:
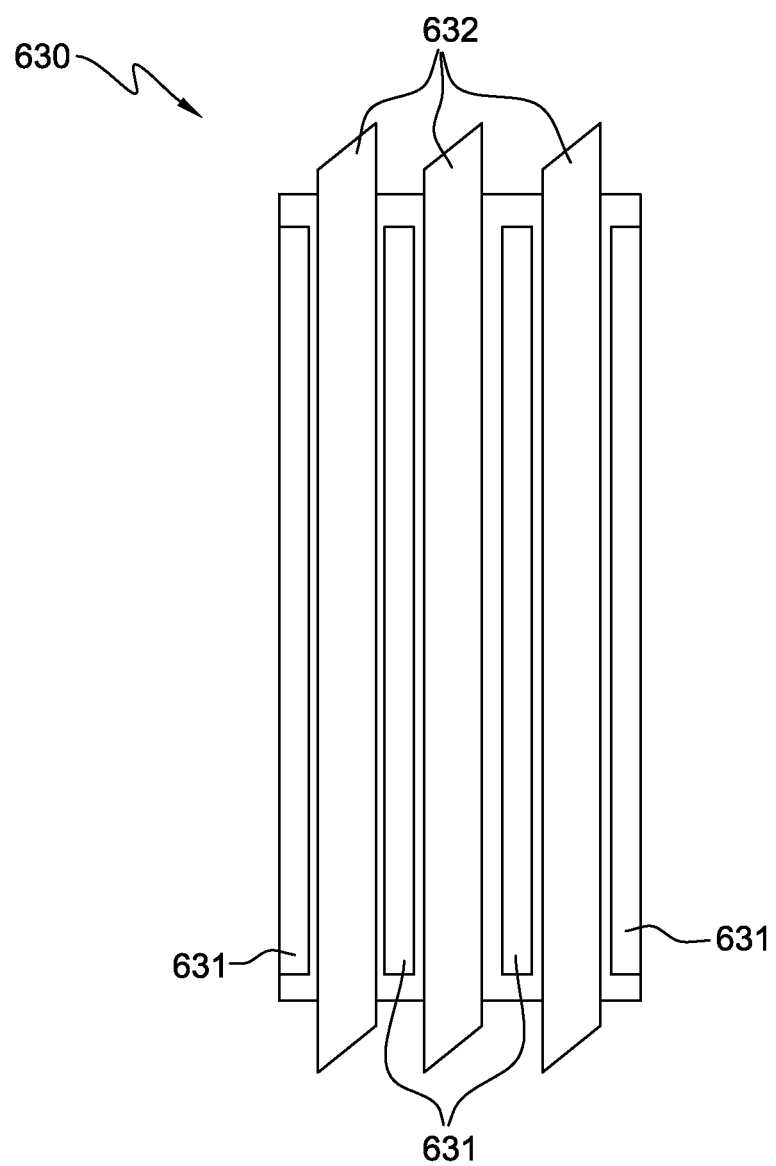
FIG. 6 depicts one example of an outdoor lighting simulation system, in accordance with one or more aspects of the present invention.

As described above, the display monitor may be controlled cooperatively with the surrounding outdoor lighting simulation system to simulate outdoor lighting patterns, including sunlight passing through a window. FIG. 6 depicts one example of an outdoor lighting simulation system. In FIG. 6, outdoor lighting simulation system 630 includes one or more light sources 631. Examples of light sources 631 include light emitting diodes (LEDs), such as high optical flux LEDs. Outdoor lighting simulation system 630 also includes components, such as movable flaps 632, for adjusting characteristics of light emitted from light sources 631. Movable flaps 632 adjust directional characteristics and provide light dampening of light emitted from light sources 631. In one example, outdoor lighting simulation system 630 provides simulated sunlight to the room as the sun travels across the sky by positioning flaps 632 to extend radially away from the center of outdoor lighting simulation system 630, while light sources 631 are activated sequentially from one side of outdoor lighting simulation system 630 to the other side during the period of daylight. In this manner, flaps 632 would direct the emitted light from light sources 631 such that the virtual daylight emitted therefrom and entering the room travels across the room from a virtual sunrise to a virtual sunset, as if real sunlight were coming through a real window located at the position of the display monitor and the outdoor lighting simulation system. Additionally or alternatively, a similar effect can be produced by positioning the flaps parallel to each other and slowly moving them in unison over the course of the virtual daytime to direct light across the room during the hours of virtual daylight.

As described above, outdoor lighting simulation system 630 is capable of simulating various sunlight conditions to mimic all times of day such as sunrise, mid-day, sunset, nighttime (as well as all times therebetween), and also weather conditions like degrees of cloudiness. It is, in some embodiments, able to simulate ambient light characteristics and behavior of outside light, including variations in brightness as the sun is covered by clouds or at sunset. Outdoor lighting simulation system 630 can include internal components allowing controllers (e.g. 160 of FIG. 1) to directly or indirectly control the brightness, color, intensity, and/or direction of light emitted from the outdoor lighting simulation system, including variations and durations of each of these properties. In order to facilitate emulating real sunlight entering through a window, the outdoor lighting simulation system can be partially or fully covered or surrounded by a shade or valances (such as flaps 632, or blinds) and provided around the display monitor, if present.

In operation, outdoor lighting simulation system 630 receives direction from one or more controllers as to the intensity, color, and direction of light to be emitted from outdoor lighting simulation system 630. This direction is based on desired lighting conditions, such as lighting conditions for providing the desired circadian rhythm cycle to the patient, as described above. In this manner, controller(s) are able control light within the patient recovery room to create the appropriate virtual daylight therein.

Figure 7:
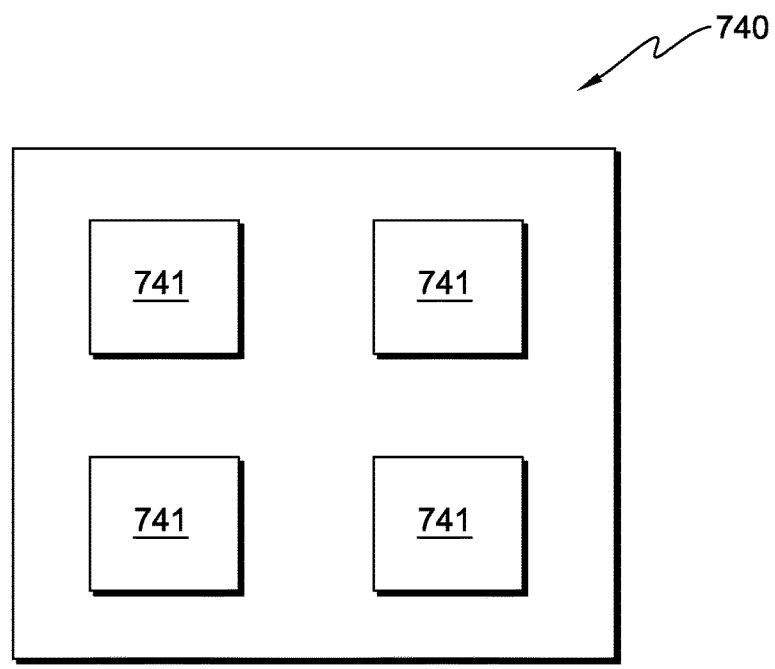
FIG. 7 depicts one example of a variable intensity ambient lighting system, in accordance with one or more aspects of the present invention.

The light provided by outdoor lighting simulation system 630 is, in some embodiments, provided in addition to, and in cooperation with, light from a variable intensity ambient lighting system (e.g. 140 of FIG. 1). An example variable intensity ambient lighting system is described in connection with FIG. 7. In FIG. 7, variable intensity ambient lighting system 740 includes one or more light sources 741 for producing variable intensity light in a patient recovery room (e.g. 101 of FIG. 1). Similar to the outdoor lighting simulation system of FIGS. 1 and 6, variable intensity ambient lighting system 740 is controllable by one or more controller(s) to provide ambient lighting of controlled brightness and/or color to correspond to the lighting conditions desired for a patient recovery room. The variable intensity light emitted from the variable intensity ambient lighting system may cooperate with, e.g., sunlight simulated by outdoor lighting simulation system 130/630 to deliver lighting conditions within the patient recovery room that are appropriate for the selected circadian rhythm cycle, as controlled by the one or more controllers. In some embodiments, such as described below, the variable intensity ambient lighting system is omitted, where the outdoor lighting simulation system is provided as the only lighting system simulating presence of natural light within the patient recovery room.

Figure 8:
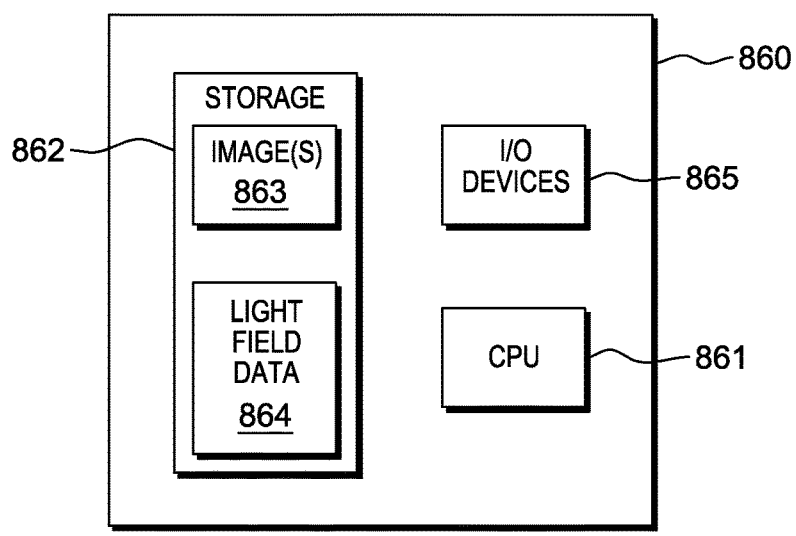
FIG. 8 depicts one example of a controller for controlling components of a therapeutic cognitive environmental psycho-physiological image system, in accordance with one or more aspects of the present invention.

FIG. 8 depicts one example of a controller for controlling components of a therapeutic cognitive environmental psycho-physiological image and light system. In FIG. 8, controller 860 includes one or more processors or CPUs 861, data storage device 862, and input/output (I/O) device(s) 865. Storage device 862 includes, in one example, stored image(s) 863 and stored light field data 864. In one embodiment, one or more controllers 860 captures, stores, & replays corresponding image and lighting content necessary to simulate a window providing a view of a scene in the outside world. Stored images 863 comprise images that are captured and stored, at least temporarily, for later display. They may include images stored by a digital video recorder, or images stored on optical storage such as a DVD or CD. Stored images 863 can also include images stored from satellite or cable channel transmissions. The stored images 863 may be stored as part of a database of images and/or videos depicting various scenes and portraying natural light characteristics having specific circadian rhythm cycles from different geographic locations on earth.

Stored light field data 864 includes data about light fields, and are used by controller 860 to control one or more components of the therapeutic cognitive environmental psycho-physiological image and light system. For instance, light field data 864 can include data that is usable to control outdoor lighting simulation system 130/630 and variable intensity ambient lighting system 140/740 to accomplish recreating lighting conditions of the recorded environmental illumination data.

In one embodiment, stored light field data 864 corresponds to at least some of the stored images. That is, light field data 864 comprises data that is used by the system (100 of FIG. 1) to reproduce or coincide with the lighting conditions at the location(s) depicted in the one or more images to which that light field data corresponds. For instance, if stored images 863 comprise a video of a beach scene, stored light field data 864 can include data that is usable by controller 860 to control outdoor lighting simulation system 130/630 and/or variable intensity ambient lighting system 140/740 to reproduce the lighting conditions of that beach scene. Light field data 864 can include data about intensity, brightness, direction, and color of light, including shadows and duration/timing information of each of these characteristics, at the location when the images were obtained. The data can be gathered from observed/measured lighting conditions over a period of time so that the stored light field data can be used by controllers to recreate, within the patient recovery room, the changes in lighting conditions that occurred at that geographic location over that period of time. The period of time could be sunrise to sunset, or any other period of time. Additionally, light field data 864 can include data about nighttime lighting conditions such as conditions caused by the presence of the moon or other environmental stimuli.

Controller 860 also comprises one or more I/O devices 865. I/O devices 865 include hardware and/or software components used by the controller to communicate with one or more components across a communications path as described above. Other examples of I/O devices include keyboards, mice, monitors, cameras, network adapters, serial connections, parallel connections, USB connections, audio/video connections, and disk drives including optical drives. In one particular example, a touch-panel I/O device is provided and the touch-panel device is used to select or specify the desired images and circadian rhythm cycle, and additionally to provide controls to allow a user (medical professional, nurse, patient, etc.) to control one or more of the components of imaging system 100. Controllers may also communicate with a nurse's station PC for remote control of the system and/or access to information regarding the system's operation, as examples.

Controllers can have dedicated function(s), for instance where one controller is adapted to capture image and lighting information data and store it, while another controller is responsible for playing back the images/video on the display monitor in a controlled fashion, and yet another controls the light provided by an outdoor lighting simulation system and variable intensity ambient lighting system as described herein to facilitate the reproduction of lighting based on the light field data. Alternatively, a single controller can perform the above functions or a set of controllers acting in cooperation with each other can collectively perform the above functions.

Figure 9:
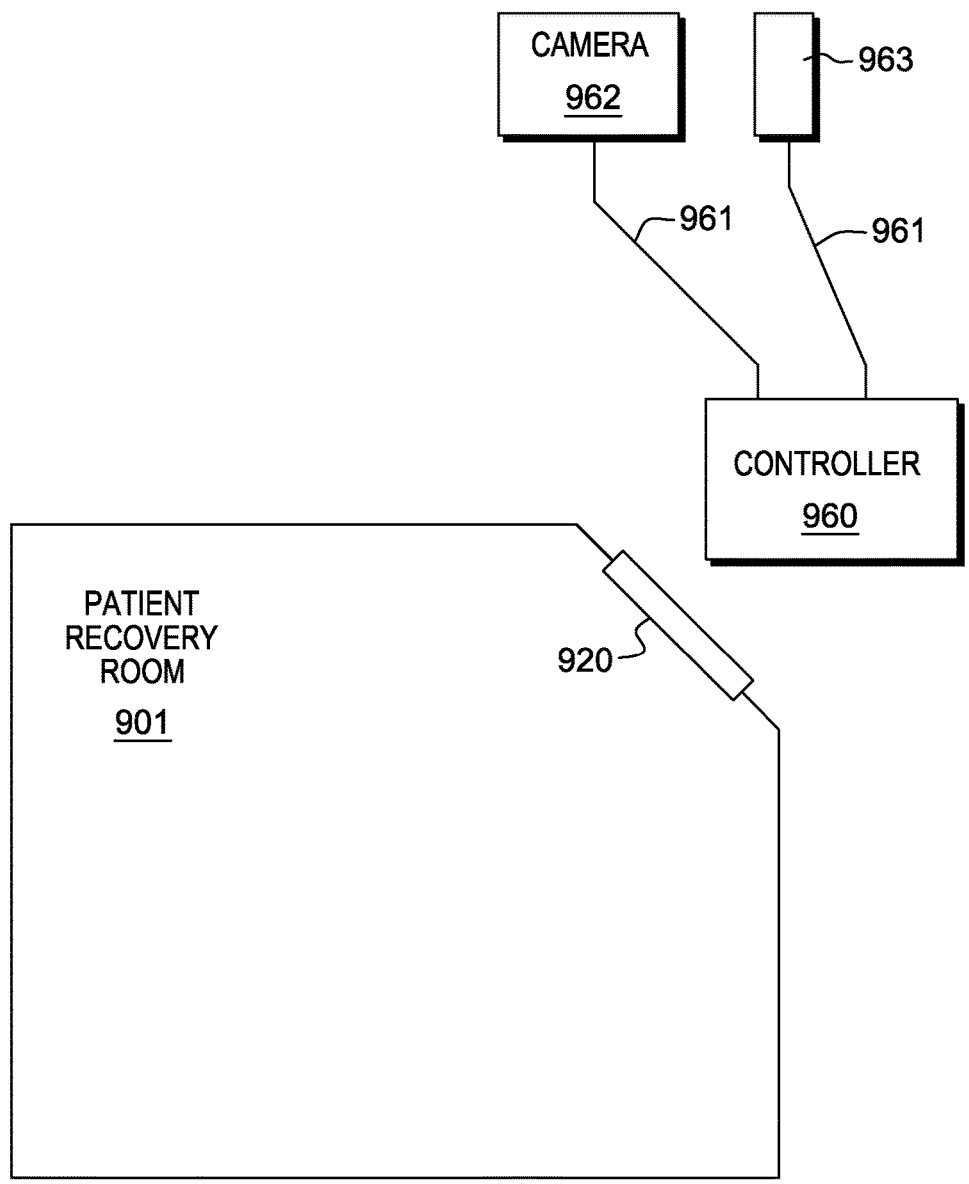
FIG. 9 depicts one example of a configuration for obtaining one or more images and light field data from an outdoor location, in accordance with one or more aspects of the present invention.

The images for display and light field data for controlling outdoor lighting simulation system and variable intensity ambient lighting system can be loaded onto to the controllers by a user, or the controllers may themselves be configured to obtain the images and light field data from external source(s). In one embodiment, controllers 160 capture/relay real-time streaming images and real-time lighting conditions corresponding to the real-time images. FIG. 9 depicts one example of a configuration for obtaining one or more images and light field data from an outside location, in accordance with an aspect of the present invention. In this example, controller(s) 960 are in communication via communication path(s) 961 with camera(s) 962 and light sensors 963. Real-time images are obtained from camera(s) 962 and associated with lighting information obtained simultaneously via light sensors 963, which are positioned next to, or in the vicinity of, camera(s) 962. This information is fed to controller 960, where, in one embodiment, they are stored as stored images and light field data (863, 864 of FIG. 8) for later use. In another embodiment, the real-time images from camera(s) 962 may be displayed in real time on a display monitor 920, while real-time light field data obtained via light sensors 963 are used to control a lighting system, such as an outdoor lighting simulation system and/or variable intensity ambient lighting system within the patient recovery room, to recreate, within that patient room and in real-time, the photometric data and lighting characteristics of the outside location where the camera and light sensors are positioned. In this embodiment, real-time light data is used to control an outdoor lighting simulation system and/or a variable intensity ambient lighting system within patient recovery room 901 for providing real-time light characteristics of the outside location, while at the same time, real-time images from the outside location are displayed on display monitor 920.

The outside location can be located proximate the patient room, such as on the roof or exterior of the building in which the patient recovery room is located. In one example, camera 962 and light sensors 963 are located proximate the patient recovery room 901, such that the patient is presented with scenes (on the display monitor) and lighting as if a real window were situated at the location of display monitor 920. In this manner, the impression and sensation is given of a real window at the particular location of the patient recovery room. Alternatively, camera 962 and/or light sensors 963 are positioned at any geographic location (indoors or outdoors) to provide distance vistas from anywhere in the world. In the case that the camera(s) are provided outdoors, weatherproof housing on cameras may be provided to prevent wear and tear and/or damage cause by environmental factors such as weather-related elements.

In one example, camera(s) 962 are part of a closed circuit camera system streaming images over a closed circuit, which includes controller 960. In this particular example, controller 960 could include a CCTV switch.

Figure 10:
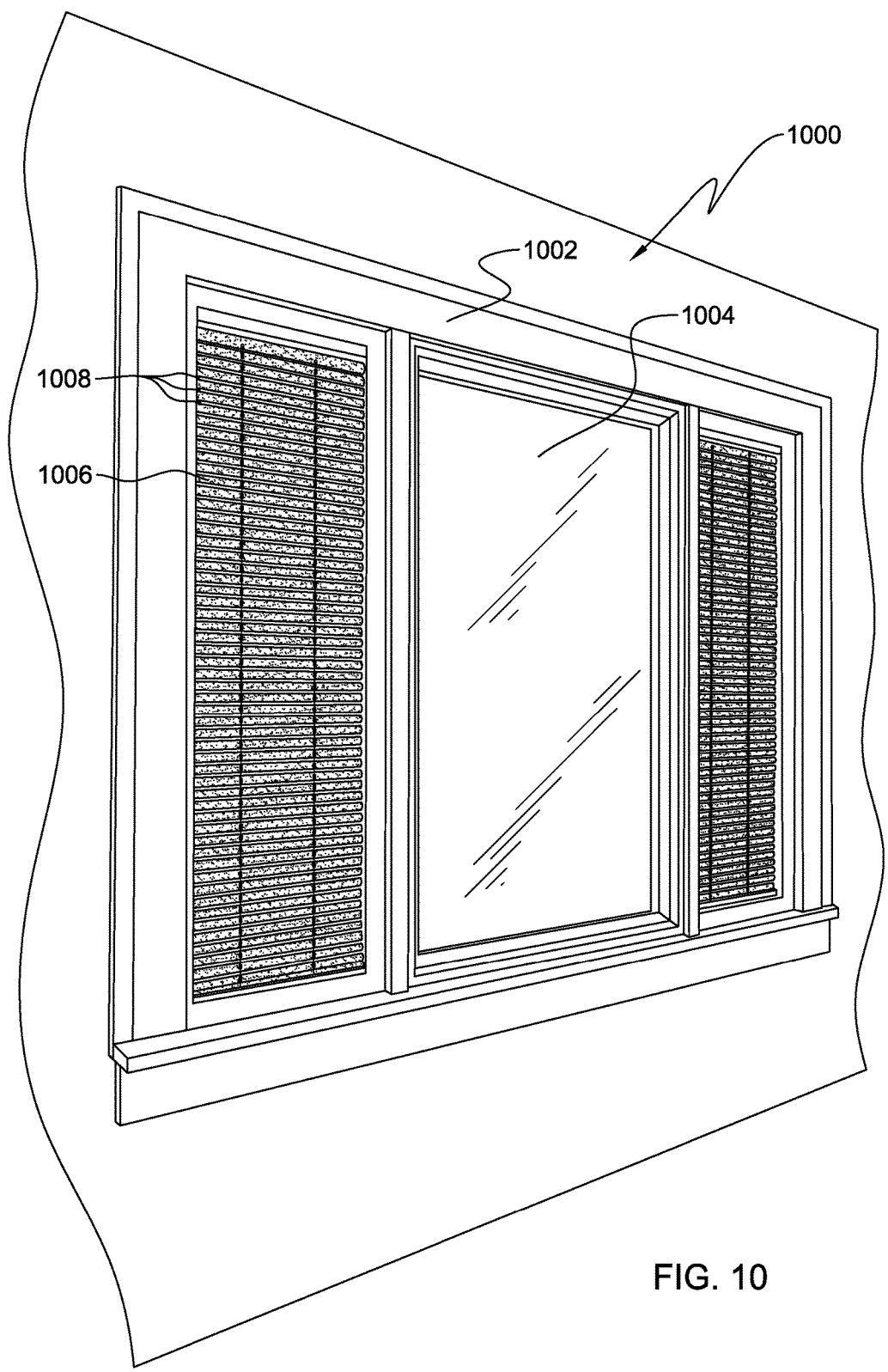
FIG. 10 depicts one example of a virtual window provided in accordance with one or more aspects of the present invention.

FIG. 10 depicts one example of a virtual window provided in accordance with one or more aspects of the present invention. In FIG. 10, virtual window 1000 is provided within a patient recovery room located in a medical facility such as a hospital, and includes a window frame 1002 defining a border around a display monitor (in this case, LCD display 1004), and a lighting system which includes, on each of the left and right sides of LCD display 1004, a set of window blinds 1006 (represented by a stipple pattern in FIG. 10) covering an underlying light panel 1008. LCD display 1004 is a 48" LCD TV monitor mounted in a vertical orientation, in this example. Blinds 1006 include multiple horizontal flaps that are spaced apart vertically for the length of light panels 1008. In this example, the blinds are partially closed (e.g. sloped downward) to dampen the light intensity emitted by light panels 1008 into the patient recovery room. In this example, the lighting system forms an outdoor lighting simulation system. Optionally, a variable intensity ambient lighting system (as described above) may or may not be provided within the patient recovery room to work in cooperation with the outdoor lighting simulation system.

In the example of FIG. 10, LCD display 1004 receives, via a controller including, for instance, a CCTV switch, a live camera feed from a camera located on the roof of the hospital in which the patient recovery room is located. As the live camera feed is received, the lighting system provides appropriate light to patient recovery room by, for instance, adjusting light panels 1008 and/or blinds 1006 to adjust the color, intensity, brightness, and/or direction of light emitted from the lighting system. In one example, this appropriate light simulates the light characteristics of the outside scene being displayed on LCD display 1004, and in this regard, light sensors may be provided alongside the outdoor camera to sense light field characteristics of the natural light, or the light field characteristics may be estimated by analyzing the real-time images being provided by the outdoor camera.

Additionally or alternatively, the appropriate light simulated by the outdoor lighting simulation system simulates other light characteristics, for instance light characteristics of a twilight scene, or any other light characteristics. In this latter regard, the appropriate light provided by the lighting system might be based on a prescribed circadian rhythm cycle for the patient.

In some embodiments, the live feed being displayed is a selected live feed from multiple available live feeds from one or more locations. For instance, there may be multiple cameras mounted around/on the hospital in which the patient recovery room is located, and the patient or medical professional can select which live feed to display on LCD display 1004, which, accordingly, selects the lighting conditions to provide within the recovery room (i.e. conditions to match the conditions displayed in the live feed).

As will be appreciated by those having ordinary skill in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system".

The computer readable medium may be a computer readable storage medium, such as, for instance, an electronic, magnetic, optical, electromagnetic, infrared or semiconductor system, apparatus, or device, or any combination thereof. More specific examples of the computer readable storage medium include for instance: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any combination thereof. In the context of this document, a computer readable storage medium may be any tangible or non-transitory medium that can contain or store program code for use by or in connection with an instruction execution system, apparatus, or device.

Figure 11:
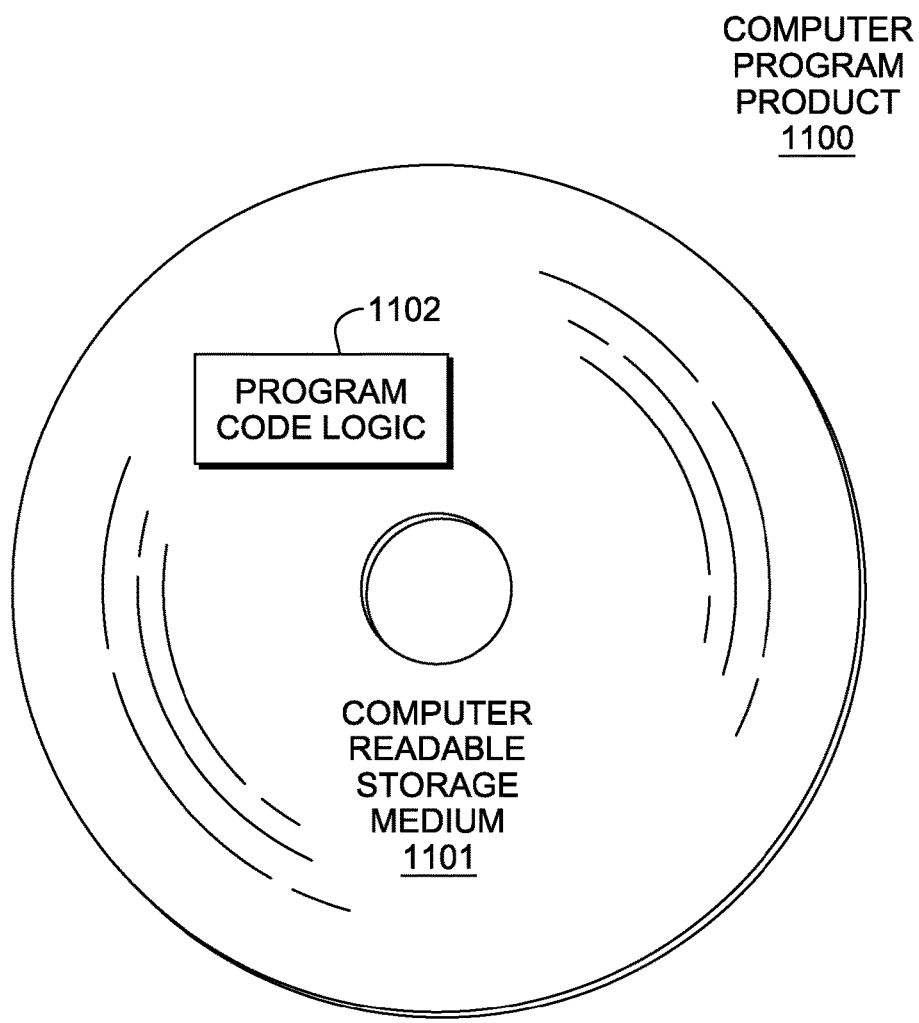
FIG. 11 depicts one embodiment of a computer program product incorporating one or more aspects of the present invention.

Referring now to FIG. 11, in one example, a computer program product 1100 includes, for instance, one or more computer readable storage medium 1101 to store computer readable program code means or logic 1102 thereon to provide and facilitate one or more aspects of the present invention.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language, C++ or the like, and conventional procedural programming languages, such as the "C" programming language, assembler or similar programming languages. The program code may execute entirely on a user's computer, partly on the user's computer, as a stand-alone software package, partly on the user's computer and partly on a remote computer or entirely on a remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention may be described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

While aspects of the invention are described in the hospital setting, other settings other than hospitals will benefit from the invention. Aspects of the invention may be valuable in the care of elderly and/or infirm people and others who have limited exposure to natural light, such as those who work night shifts. Aspects of the invention may be beneficial for employers and employees, to influence performance, productivity, absenteeism, and 'presenteeism' in a favorable manner. In general, aspects of the invention may be useful to improve mood, cognition, energy, performance, resilience, and to reduce cardiovascular, cancer, and other health risks.

What is claimed is:

1. A system comprising:
a display monitor in an environment configured for a patient;
a lighting system in the environment comprising an outdoor lighting simulation system and an ambient lighting system; and
at least one controller, the at least one controller configured to perform:
obtaining a patient goal or recovery treatment plan tailored to health-related recovery of the patient;
identifying, based on the obtained patient goal or recovery treatment plan, at least one appropriate circadian rhythm cycle to promote the health-related recovery of the patient;
selecting a circadian rhythm cycle from the at least one appropriate circadian rhythm cycle; and
treating the patient through provision of at least one therapeutic benefit promoting the health-related recovery of the patient, the treating comprising:
controlling display of one or more images on the display monitor;
controlling the lighting system, the controlling the lighting system providing lighting of variable characteristics from the lighting system;
automatically cooperatively controlling the display of the one or more images on the display monitor together with the lighting of variable characteristics from the lighting system;
presenting a simulated view simulating presence of an actual window within the environment with the one or more images being a view of an external environment through the actual window, the simulated view varying the lighting conditions depicted in the one or more images to simulate lighting variations of the external environment that would occur within a period of time according to the selected circadian rhythm cycle;
and varying at least brightness and direction characteristics of the lighting from the outdoor lighting simulation system and varying at least brightness characteristics of the lighting from the ambient lighting system within the environment to simulate lighting variations that would normally occur within the environment during the period of time of the selected circadian rhythm cycle due to the lighting variations of the external environment passing through the actual window and into the environment, the controlling the lighting system and the varying the characteristics of the lighting of the outdoor lighting simulation system and the ambient lighting system thereby providing control of the lighting within the environment from the lighting system to conform to the selected circadian rhythm cycle that would be experienced within the environment from the lighting of the external environment passing through the actual window.

2. The system of claim 1, wherein treating the patient further comprising varying color characteristics of the lighting from the lighting system within the environment to simulate lighting variations that would normally occur within the environment during the period of time of the selected circadian rhythm cycle due to the lighting variations of the external environment passing through the actual window and into the environment.

3. The system of claim 1, wherein the environment comprises a patient recovery room and the patient is a patient within the patient recovery room, wherein the controlled light within the patient recovery room facilitates entraining the patient's circadian rhythm cycle to a prescriptively-selected circadian rhythm cycle to promote healing of the patient, and wherein the one or more images are selected based on the prescriptively-selected circadian rhythm cycle for display on the display monitor.

4. The system of claim 3, wherein the at least one controller is further configured to perform varying both (i) lighting within the patient recovery room provided by the lighting system across a cycle extending between a virtual sunrise and a virtual sunset, and (ii) display of the one or more images, which depict lighting characteristics of the virtual sunrise and virtual sunset, on the display monitor, thereby simulating, over a period of time, the presence of the actual window and provision therethrough of light patterns and visual images between actual sunrise and actual sunset at a location depicted in the one or more images displayed on the display monitor, and wherein the prescriptively-selected circadian rhythm cycle comprises lighting conditions corresponding to light patterns occurring between actual sunrise and actual sunset at the location depicted in the one or more images.

5. The system of claim 1, wherein the at least one appropriate circadian rhythm cycle comprises at least one prescriptively-selected circadian rhythm cycle in accordance with the patient goal or recovery treatment plan.

6. The system of claim 1, wherein the environment comprises a patient recovery room and the patient is a patient within the patient recovery room, and wherein the system further comprises an ultraviolet light source within the patient recovery room, wherein the at least one controller is further configured to perform controlling discharge of ultraviolet light from the ultraviolet light source to the patient to facilitate production of Vitamin D by the patient that would normally occur during the period of time of the selected circadian rhythm cycle due to the lighting variations of the external environment passing through the actual window and into the environment.

7. The system of claim 1, wherein the at least one controller is further configured to perform:
  (i) selecting as the one or more images displayed on the display monitor real-time streaming video images of an outdoor area proximate the environment as the external environment; and
  (ii) varying at least the brightness and direction characteristics of the lighting from the outdoor lighting simulation system and varying at least brightness characteristics of the lighting from the ambient lighting system to simulate real-time natural light present at the outdoor area proximate the environment entering the environment through the actual window, the selecting and varying thereby providing a light and image experience within the environment to conform to the selected circadian rhythm cycle that would be experienced within the environment from the naturally occurring light passing through the actual window.

8. The system of claim 1, wherein the outdoor lighting simulation system is positioned adjacent to the display monitor within the environment.

9. A method comprising:
  providing a display monitor and a lighting system in an environment configured for a patient, the lighting system comprising an outdoor lighting simulation system and an ambient lighting system; and
  providing at least one controller, the at least one controller configured to perform:
    obtaining a patient goal or recovery treatment plan tailored to health-related recovery of the patient;
    identifying, based on the obtained patient goal or recovery treatment plan, at least one appropriate circadian rhythm cycle to promote the health-related recovery of the patient;
    selecting a circadian rhythm cycle from the at least one appropriate circadian rhythm cycle; and
    treating the patient through provision of at least one therapeutic benefit promoting the health-related recovery of the patient, the treating comprising:
      controlling display of one or more images on the display monitor;
      controlling the lighting system, the controlling the lighting system providing lighting of variable characteristics from the lighting system;
      automatically cooperatively controlling the display of the one or more images on the display monitor together with the lighting of variable characteristics from the lighting system;
      presenting a simulated view simulating presence of an actual window within the environment with the one or more images being a view of an external environment through the actual window, the simulated view varying the lighting conditions depicted in the one or more images to simulate lighting variations of the external environment that would occur within a period of time according to the selected circadian rhythm cycle; and
      varying at least brightness and direction characteristics of the lighting from the outdoor lighting simulation system and varying at least brightness characteristics of the lighting from the ambient lighting system within the environment to simulate lighting variations that would normally occur within the environment during the period of time of the selected circadian rhythm cycle due to the lighting variations of the external environment passing through the actual window and into the environment, the controlling the lighting system and the varying characteristics of the lighting of the outdoor lighting simulation system and the ambient lighting system thereby providing control of the lighting within the environment from the lighting system to conform to the selected circadian rhythm cycle that would be experienced within the environment from the lighting of the external environment passing through the actual window.

10. The method of claim 9, wherein the at least one appropriate circadian rhythm cycle comprises at least one prescriptively-selected circadian rhythm cycle in accordance with the patient goal or recovery treatment plan.

11. The method of claim 9, wherein the at least one controller is further configured to perform:
  (i) selecting as the one or more images displayed on the display monitor real-time streaming video images of an outdoor area proximate the environment as the external environment; and
  (ii) varying at least the brightness and direction characteristics of the lighting from the outdoor lighting simulation system and varying at least brightness characteristics of the lighting from the ambient lighting system to simulate real-time natural light present at the outdoor area proximate the environment entering the environment through the actual window, the selecting and varying thereby providing a light and image experience within the environment to conform to the selected circadian rhythm cycle that would be experienced within the environment from the naturally occurring light passing through the actual window.

12. A method comprising:
providing a therapeutic environment for a patient, the providing comprising:
obtaining a patient goal or recovery treatment plan tailored to health-related recovery of the patient;
identifying, based on the obtained patient goal or recovery treatment plan, at least one appropriate circadian rhythm cycle to promote the health-related recovery of the patient;
selecting a circadian rhythm cycle from the at least one appropriate circadian rhythm cycle; and
treating the patient through provision of at least one therapeutic benefit promoting the health-related recovery of the patient, the treating comprising:
controlling display of one or more images on a display monitor in the environment;
controlling a lighting system in the environment comprising an outdoor lighting simulation system and an ambient lighting system, the controlling the lighting system providing lighting of variable characteristics from the lighting system;
automatically cooperatively controlling the display of the one or more images on the display monitor together with the lighting of variable characteristics from the lighting system;
presenting a simulated view simulating presence of an actual window within the environment with the one or more images being a view of an external environment through the actual window, the simulated view varying the lighting conditions depicted in the one or more images to simulate lighting variations of the external environment that would occur within a period of time according to the selected circadian rhythm cycle; and
varying at least brightness and direction characteristics of the lighting from the outdoor lighting simulation system and varying at least brightness characteristics of the lighting from the ambient lighting system within the environment to simulate lighting variations that would normally occur within the environment during the period of time of the selected circadian rhythm cycle due to the lighting variations of the external environment passing through the actual window and into the environment, the controlling the lighting system and the varying the characteristics of the lighting of the outdoor lighting simulation system and the ambient lighting system thereby providing control of the lighting within the environment from the lighting system to conform to the selected circadian rhythm cycle that would be experienced within the environment from the lighting of the external environment passing through the actual window.

13. The method of claim 12, wherein the providing further comprises:

(i) selecting as the one or more images displayed on the display monitor real-time streaming video images of an outdoor area proximate the environment as the external environment; and
(ii) varying at least the brightness and direction characteristics of the lighting from the outdoor lighting simulation system and varying at least brightness characteristics of the lighting from the ambient lighting system to simulate real-time natural light present at the outdoor area proximate the environment entering the environment through the actual window, the selecting and varying thereby providing a light and image experience within the environment to conform to the selected circadian rhythm cycle that would be experienced within the environment from the naturally occurring light passing through the actual window.

14. The method of claim 12, wherein the identified at least one appropriate circadian rhythm cycle is identified from a plurality of pre-programmed circadian rhythm cycles available for selection.

15. The method of claim 12, wherein the automatically cooperatively controlling the display of the one or more images on the display monitor together with the lighting of variable characteristics from the lighting system comprises continuously adjusting the one or more images by filter or other image processing when displayed on the display monitor during a timeframe to mimic lighting conditions within the environment based on the selected circadian rhythm cycle that would result from the lighting of the external environment passing through the actual window.

16. A computer program product comprising:
a non-transitory storage medium readable by a processor and storing instructions for execution by the processor to perform a method comprising:
providing a therapeutic environment for a patient, the providing comprising:
obtaining a patient goal or recovery treatment plan tailored to health-related recovery of the patient;
identifying, based on the obtained patient goal or recovery treatment plan, at least one appropriate circadian rhythm cycle to promote the health-related recovery of the patient;
selecting a circadian rhythm cycle from the at least one appropriate circadian rhythm cycle; and
treating the patient through provision of at least one therapeutic benefit promoting the health-related recovery of the patient, the treating comprising:
controlling display of one or more images on a display monitor in the environment;
controlling a lighting system in the environment comprising an outdoor lighting simulation system and an ambient lighting system, the controlling the lighting system providing lighting of variable characteristics form the lighting system;
automatically cooperatively controlling the display of the one or more images on the display monitor together with the lighting of variable characteristics from the lighting system;
presenting a simulated view simulating presence of an actual window within the environment with the one or more images being a view of an external environment through the actual window, the simulated view varying the lighting conditions depicted in the one or more images to simulate lighting variations of the external environment that would occur within a period of time according to the selected circadian rhythm cycle; and varying at least brightness and direction characteristics of the lighting from the outdoor lighting simulation system and varying at least brightness characteristics of the lighting from the ambient lighting system within the environment to simulate lighting variations that would normally occur within the environment during the period of time of the selected circadian rhythm cycle due to the lighting variations of the external environment passing through the actual window and into the environment, the controlling the lighting system and the varying the characteristics of the lighting of the outdoor lighting simulation system and the ambient lighting system thereby providing control of the lighting within the environment from the lighting system to conform to the selected circadian rhythm cycle that would be experienced within the environment from the lighting of the external environment passing through the actual window.

* * * * *